United States Patent
Newton et al.

(10) Patent No.: US 6,534,549 B1
(45) Date of Patent: Mar. 18, 2003

(54) CONTROLLED RELEASE FORMULATIONS

(75) Inventors: John Michael Newton, London (GB); Lee Fung Siew, Dublin (IE)

(73) Assignee: BTG International Limited, London (GB)

( * ) Notice: Subject to any disclaimer, the term of this patent is extended or adjusted under 35 U.S.C. 154(b) by 0 days.

(21) Appl. No.: 09/516,253

(22) Filed: Mar. 1, 2000

Related U.S. Application Data

(63) Continuation of application No. PCT/GB98/03178, filed on Oct. 23, 1998.

(30) Foreign Application Priority Data

Oct. 23, 1997 (GB) .............................................. 9722426

(51) Int. Cl.[7] .......................... A61K 47/32; A61K 9/00; A61K 9/14; A61K 9/16
(52) U.S. Cl. .................... 514/772.4; 424/400; 424/489; 424/490; 424/493; 424/495
(58) Field of Search ....................... 514/772.4; 424/497, 424/400, 489, 490, 493, 495

(56) References Cited

U.S. PATENT DOCUMENTS 5,294,448 A * 3/1994 Ring et al. .................. 424/497

FOREIGN PATENT DOCUMENTS

WO         WO91/07949         6/1991

OTHER PUBLICATIONS

Milojevic et al. "Amylose as a coating for drug delivery to the colon: Preparation and in vitro evaluation using 5–aminosalicyclic acid pellets," Journal of Controlled Release, vol. 38, No. 1, pp 75–84, 1996.*

S. Milojevic Et Al: "amylose as a coating for drug delivery to the colon: preparation and in vitro evaluation using: 5–aminosalicyclic acid pellets" Journal of Controlled Release, : vol. 38, No. 1, Jan. 1996, pp. 75–84, XP000543711 : Amsterdam/NL.

S. Narisawa Et Al.: "porosity–controlled ethylcellulose film coating. I. formation of porous ethylcellulose film in the casting process and factors affecting film–density" Chemical : & Pharmaceutical Bulletin, vol. 41, No. 2, Feb. 1993, : pp. 329–334, XP000354418 Tokyo/JP.

Newton, J.M., "Suitability of Mixed Amylose/Ethylcellulose Films as . . . ," Department of Pharmaceutics, The School of Pharmacy, University of London, United Kingdom.

* cited by examiner

Primary Examiner—Thurman K. Page
Assistant Examiner—Blessing Fubara
(74) Attorney, Agent, or Firm—Nixon & Vanderhye

(57) ABSTRACT

A method for producing a controlled release composition is provided. A solution of a film-forming composition comprising a mixture of a substantially water-insoluble film-forming polymer and amylose in a solvent system comprising (1) water and (2) a water-miscible organic solvent which on its own is capable of dissolving the film-forming polymer is contacted with an active material and the resulting composition dried. The weight ratio of amylose to film-forming insoluble polymer in the film-forming composition is in the range 1:2 to 3:2 and the organic solvent comprises at least 50% by weight of the solvent system. The composition is particularly suitable for delivering therapeutic agents to the colon.

17 Claims, 6 Drawing Sheets

CONTROLLED RELEASE FORMULATIONS

This is a continuation of application No. PCT/GB98/03178 filed Oct. 23, 1998.

The present invention relates to controlled, usually delayed release formulations, where the release characteristics are controlled by a polymer.

BACKGROUND OF THE INVENTION

In U.S. Pat. No. 3,499,962 and GB 1,072,795 colloidal amylose solutions, prepared under conditions of high pressure and temperature, were used to coat or encapsulate particles used, for example, in nutritional, pharmaceutical, cosmetic and agricultural applications. Encapsulation of active materials at lower temperatures and pressures required the presence of a salt such as an aqueous alkali metal hydroxide. These conditions are not conductive to the encapsulation of sensitive or reactive particles that are unstable when subjected to heat, light or conditions substantially different to those encountered in certain physiological environments.

The ability of faecal micro-organisms present in the colon to degrade amylose has been disclosed by Cairns et al, J.Cer.Sci.,12,203–206,(1990). The preparation and use of formulations containing amylose is described in U.S. Pat. Nos. 5,294,448 and 5,108,758. The preparation of amylose solutions has been discussed by Ring et al., Macromolecules, 1985, 18,182 where an aqueous dispersion of amylose in complexed form was heated with a $C_{1-5}$ alcohol to between 70° C. and 90° C. Amylose solutions prepared using similar techniques were used in the formulation of those compositions described in U.S. Pat. Nos. 5,294,448 and 5,108,758, EP-A-0502032 and GB-A-2220350.

SUMMARY OF THE INVENTION

The present invention provides a method for producing a controlled release composition comprising an active ingredient and a film formed from a film-forming composition comprising a mixture of a substantially water-insoluble film-forming polymer and amylose, the method comprising contacting the active ingredient with a solution of the film-forming composition in a solvent system comprising (1) water and (2) a water-miscible organic solvent which on its own is capable of dissolving the film-forming polymer and removing the water and organic solvent, wherein the weight ratio of amylose to film-forming polymer is in the range 1:2 to 3:2 and the solvent system contains at least 50% w/w organic solvent.

The temperature used in the process generally need be no higher than 60° C. and may often be ambient. Preferably the temperature is in the range 20 to 40° C.

The controlled release composition formed according to the method of the present invention finds particular application in the delivery of an active material to the colon. The composition has been found to be substantially resistant to the conditions present in the stomach and the small intestine but is susceptible to attack by the micro-organisms of the colon.

The present invention should generally be accompanied by solvent recovery. Thus during the step in which the solvent is removed by evaporation, the vapour, which generally comprises a mixture of water vapour and solvent vapour, should be recovered, condensed and the solvent preferably recycled in the process. The condensed solvent mixture may be separated to render the solvent substantially free of water, or a mixture of water and solvent of known solvent concentration may be reused in the process.

Suitable condenser equipment for solvent removal and recovery from an active ingredient coating station is known and is available, for instance from the manufacturers Glatt.

The organic solvent which is used in the invention is selected for its miscibility with water. It is preferably sufficiently water-miscible such that a homogeneous blend containing 10 to 90% of an organic solvent at room temperature and pressure can be formed. The solvent should also be selected for its ability to solubilise the film-forming polymer and the amylose. Thus those components should be soluble in the organic solvent (in the absence of water) at a concentration of at least 5 or 6%, preferably at least10%, at a temperature of 40° C.

Suitable solvents are $C_{2-10}$-alkanols, ethers, alcohol ethers and esters of mono or higher base carboxylic acids, generally with mono alkanols, which are liquid at room temperature and miscible with water in the stated amounts. Suitable esters are, for instance, esters of lactic acid, such as ethyl lactate. Preferably the solvent is a $C_{2-4}$ alkanol, and is most preferably selected from ethanol and propanol.

The relative amounts of solvent and water required for use in the solvent system of the present invention have been found to depend upon the nature of both the organic solvent used and the water-insoluble polymer. The organic solvent comprises at least 50% by weight (w/w) of the solvent system, preferably between 60 and 90% of the solvent system. By way of example, when ethyl cellulose is used as the insoluble polymer, the organic solvent system used in the preparation of the film-forming composition preferably contains at least 60% by weight organic solvent when propanol is used and at least 70% by weight organic solvent when ethanol is used.

The film-forming compositions of choice used in the method of the present invention are those which give rise to films in which the amylose is present in the glassy state. Films comprising glassy amylose have been found to be resistant to degradation by both the stomach and the amylase enzymes of the small intestine, but have been found to be susceptible to attack by the micro-organisms present in the colon.

Glassy amylose is one of the two forms of predominantly amorphous amylose, the other being a rubbery form.

Amylose exists in its glassy state below the glass transition temperature (Tg). Rising through this temperature, there is a sharp increase in the heat capacity of the amylose of $0.5 \pm 0.15 \, Jg^{-1}K^{-1}$ (joules per gram per degree Kelvin). This heat capacity increment allows the Tg to be identified and can be measured by differential scanning calorimetry. Examples of procedures for obtaining Tg values and earlier literature references to such procedures are given in Orford et al, Int.J.Biol.Macromol., 1989,11,91.

The particular Tg of a given preparation of amylose depends upon its purity and other properties. Thus, for example, the theoretical Tg for pure, dry amylose may be predicted to be 210° C. but the presence of water depresses this figure: with 10% w/w of water the Tg is 80° C. and at 20% w/w of water it is 7° C. It has been found that α-amylolytic enzymes such as those present in the small intestine do not readily degrade glassy amylose and this effect is still apparent at up to 20° C. above the Tg. Such materials have been found to be sufficiently insoluble in aqueous media over the pH range 1–9 at 37° C. to be resistant to degradation in the stomach or intestine. They are, however, degraded by faecal micro-organisms present in the colon.

The ability of glassy amylose to provide the required delayed release characteristics is not lost immediately the glassy amylose passes through the Tg and films containing amylose which has been produced in the glassy condition at temperatures less than the Tg may therefore then be utilized at the Tg or at temperatures slightly higher than the Tg as well as at temperatures less than the Tg, whilst still retaining its glassy properties. However, the glassy amylose present in the films formed from the film-forming compositions used according to the method of the present invention preferably has a Tg of no more than 20° C. below the temperature at which use of the composition is envisaged, i.e. at body temperature of about 37° C., i.e. more than or equal to 17° C., and is preferably more than or equal to about 30° C. or, more preferably, more than or equal to about 40° C. The Tg can be predetermined by controlling the amount of water in it. This can be achieved by varying the concentration of the amylose in the film-forming composition.

The ultimate test of the suitability of a particular sample of amylose in a film formed under any given conditions is of course its ability to resist hydrolytic degradation under aqueous conditions, particularly at a pH of 1–9 and a temperature of 37° C., and conveniently also to resist enzymatic degradation in the presence of the digestive enzymes such as normally occur in the stomach and the small intestine, but to undergo enzymatic degradation in the presence of amylose-cleaving enzymes such as are provided by the microbial flora normally present in the large intestine.

Films comprising amylose in the glassy state may conveniently be prepared from the film-forming compositions used in the method of the present invention by forming a gel by casting or spraying and drying that gel. The gel forms by a phase separation which produces a concentrated polymer-rich phase and a polymer-poor phase. The polymer-rich phase may have only, say 10% w/w water and hence be glassy at room temperature, even though the whole gel may contain up to 50% of water. The whole preparation may be dried if necessary or desirable at between 20 to 80° C., and more preferably between 20 to 40° C. in air or in an inert atmosphere such as nitrogen.

The amylose used in the film-forming composition may be prepared from any suitable source although it is preferably prepared from starch, for example cereal starch or tuber starch or starch from pulses, for example smooth-seeded pea starch, conveniently by precipitation from aqueous solution as a complex with an alcohol, for example 1-butanol, methanol, ethanol, propan-1-ol, propan-2-ol, pentanol, 2-methylbutan-2-ol or 2-methylbutan-1-ol as described by Ring et al., Macromolecules, 1985, 18, 182. The alcohol may conveniently then be removed from an aqueous dispersion of that complex by blowing through a suitable heated inert gas, for example nitrogen.

It will be appreciated that the presence of other materials in admixture with the glassy amylose in the film formed will detract from the selective nature of the degradation of this material as between the stomach and small intestine and the large intestine. It is preferred therefore that the glassy amylose in the film is substantially free (i.e. contains no more than 20% by weight and preferably no more than 10% or 5% by weight) of any material which is susceptible to digestion in the stomach or small intestine. In particular the glassy amylose preferably contains no more than 10% or 5% by weight of amylopectin, for example 1 or 2% or less, and conveniently also of any material containing glucoside linkages of the type found in amylopectin.

Moreover it is preferred that the glassy amylose in the film formed from the film-forming composition does not contain hydroxy groups in derivative form and, if any derivatization is present that this is conveniently to an extent of no more than 10% of the hydroxy groups present, in particular no more than 4 or 5% and particularly 1 or 2% less.

A convenient test for the purity of the amylose is provided by its iodine binding ability in a standard assay procedure such as is described by Banks et al, Starke, 1971, 23, 118. Thus pure, underivativized amylose binds with iodine to a level of about 19.5% w/w (i.e. 19.5±0.5% w/w) whereas the other main starch polysaccharide, amylopectin, binds less than 2.0% w/w and derivatization of the amylose will also reduce this binding ability. Conveniently therefore the amylose used in the present intention binds with iodine to a level of 15.0%±0.5% w/w, or above, preferably to a level of 18.0%±0.5% w/w or above, and particularly to a level of 19.5±0.5% w/w.

The molecular weight of the amylose used in the invention may conveniently be at least 20000 g/mol (or daltons) and is preferably higher so that it is advantageous to use amylose with a molecular weight of at least 100000, 200000, 300000, 400000 or 500000 g/mol depending on the particular circumstances.

Although there is a preference for the use of film-forming compositions that can be used to form films containing glassy amylose in the controlled release compositions of the present invention it is also possible to use film-forming compositions that give rise to films containing rubbery amylose. Preparation of films containing rubbery amylose may be conveniently be brought about by the addition of a plasticiser to the film-forming composition. The addition of a plasticiser conveniently leads to the formation of films containing amylose which is rubbery rather than glassy at ambient temperature since the plasticiser can depress the Tg of amylose in the film which would otherwise be glassy to some tens of degrees, i.e. 10°, 20°, 30° C. or more, below ambient temperature. Despite the latitude of up to 20° C. above the Tg for the retention of glassy characteristics by the film (mentioned hereinbefore) the amylose in the film may well then be rubbery at physiological temperature if not also at ambient temperature. Films containing rubbery amylose are however also of value, particularly when prepared with a water soluble plasticiser since such plasticisers will tend to be leached out in an aqueous environment to produce a porous amylose material. It will be appreciated, therefore, that it may be appropriate for reasons of aiding the coating procedure, controlling permeability or otherwise to add a plasticiser to the film-forming composition.

The film-forming compositions used in the method of the present invention are prepared by admixing a solution of the water insoluble polymer in an organic solvent with an aqueous dispersion of an amylose-butanol complex. The relative amounts in which the two component systems are mixed will depend upon the solid ratios of amylose and the insoluble polymer required in the final film. Suitably solutions containing between 2 and 25% w/w insoluble polymer, preferably between 2 and 8% w/w and especially between 3 and 5% w/w insoluble polymer in an organic solvent are mixed with an aqueous dispersion containing between 3 and 12% w/w of an amylose-butanol complex, preferably between 3 and 8% w/w and especially between 3 and 6% w/w. It may be necessary to concentrate the amylose-butanol dispersion to an appropriate concentration before mixing. The solutions are mixed and stirred until fully blended. The resultant solution is then passed through a sieve to remove agglomerates.

The film-forming composition thus prepared typically comprises between 2 and 8% w/w of film-forming solids in the solvent system, preferably between 3 and 6% w/w and especially between 4 and 5% w/w. The films can be prepared by casting or spraying the film-forming composition at a temperature of between 20 and 60° C. Preferably the films are formed by spraying the compositions onto the active material, the active material being maintained at a temperature of between 20 and 40° C., preferably between 30 and 40° C. and especially between 35 and 40° C. during the spraying process.

The substantially water-insoluble film-forming polymer should be water insoluble, as well as insoluble in aqueous acidic and alkaline environments. Thus the solubility of the film-forming polymer in water at room temperature should be less than 10%. The level of solubility in aqueous acidic medium at a pH 1 should be less than about 1% and in aqueous alkaline medium at a pH of 7.2 should be less than about 1%. The polymer should, on the other hand, be sufficiently soluble in the coating composition such that suitable coating/protective film formation can be achieved. The polymer should thus have a solubility of at least 5% in the organic solvent (in the absence of water) selected for the liquid composition.

Suitable film-forming materials are preferably water-insoluble cellulosic or acrylic polymer materials. Mixtures of different cellulosic or acrylic polymer materials may be used. The use of ethyl cellulose as a film-forming polymer is especially preferred.

Although the cellulose materials are the preferred film-forming materials for use as the outer coating, acrylic polymer materials may also be employed in the compositions of the present invention either alone or in admixture with a cellulose material. In particular, both acrylate and methacrylate polymers may be used and especially copolymers thereof, the esterifying groups in these polymers being of various types, for example of $C_{1-18}$ alkyl groups.

A preferred molecular weight range for the film-forming cellulose materials is 42,000 to 280,000 g/mol (or daltons) and for the film-forming acrylic polymer materials is 150,000 to 250,000 g/mol (or daltons) but materials with molecular weights outside these ranges, for example of a higher molecular weight, can be used where appropriate.

The degradation of the cellulose materials in vivo is in general not pH dependent and it is preferred that this is also true for the acrylate materials. This may be achieved by the selection of appropriate forms of side chain on the main polymer chain, in particular of side chains which have a low negative charge or preferably which are uncharged, as opposed to those having a positive charge. Preferred forms of acrylate materials are those marketed by Dumas (UK) Limited of Tunbridge Wells under the Trade Mark Eudragit, particularly the materials Eudragit L whose degradation is independent of pH. The preferred cellulose materials, ethyl cellulose, is marketed by the Dow Chemical Company and Shinetsu Chemical Products under the Trade Mark Ethocel.

It has been found that the ability of a dosage form coated according to the method of the present invention to resist degradation in the stomach and small intestine but to release the active material in the colon depends, in part, upon the ratio of the amylose to insoluble polymer in the film formed; the thickness of the film and the solubility of the active material. Therefore, by varying the ratio of amylose to insoluble polymer in the film-forming composition as well as the coat thickness of the film formed it is possible to achieve efficient release in the colon of a range of active materials of differing solubilities.

The ratio of the amylose to the film-forming polymer in the process should be in the range 1:2 to 3:2, preferably in the range 2:3 to 3:2, for instance about 1:1. Where the level of amylose is higher than the upper limit, it is found that the films mechanical characteristics may be inadequate. Where the amount of amylose is lower, the degradation of the amylose in the desired location for release (for instance the colon) may be inadequate.

As indicated above it may be desirable to incorporate a plasticiser into the blend of amylose and film-forming polymer in order to facilitate formation of the film, control the porosity and improve the mechanical properties of the film. The amount of plasticiser used will depend upon the nature of the insoluble polymer.

Examples of suitable plasticiser, particularly in the case of the cellulose materials, are dicarboxy-acid and tricarboxy-acid esters such as triethylcitrate, glycerol triacetate, acetyl tributylcitrate, tributylcitrate, triacetin and dibutyl sebacate. The proportions of substantially insoluble polymer, amylose and plasticiser can be varied according to the nature of the materials used to give a coating with the required delayed and controlled release and porosity characteristics. Ethylcellulose can be plasticised with both hydrophobic and hydrophilic plasticisers.

As indicated above, the thickness of the film also influences the rate at which an active material is released from a dosage form. Depending upon the solubility of the active material in the dosage form, release is generally slower when thicker films are employed. Thicker films are also required when highly soluble active materials are employed in order to prepare a dosage form in which the release of active material in the colon can be adequately controlled.

As regards thickness, a suitable value can be arrived at by routine experimentation but, by way of guidance, it may be stated that a thickness in the range of 2 to 50 μm is often preferred, especially in the range 20 to 50 μm, for example about 40 μm. However, it will be appreciated that, particularly when plasticiser are incorporated into the coat, a wide range of variation of thickness is possible including sometimes thicknesses greater than those quoted. Coat thickness can also be defined as the total weight gain (TWG); this is the percentage increase in weight of the active material upon coating. It is preferred that the TWG is in the range 3% to 20%, preferably 5% to 15% and especially about 9 to 11%.

As well as delayed release of at least substantial amounts of the active ingredient until the composition reaches the colon, the nature of the amylose in the film is important in providing a slow release barrier and controlling the degradation thereof by micro-organisms (microbial flora) thereby to control release of the active material once the composition reaches the colon. Thus some controlled release can be effected in the small intestine by control of the amylose employed.

Control can therefore be exercised over release of the active ingredient with respect to time by varying one or more of the parameters controlling release, e.g. coat thickness, method of coating and ratio of coating ingredients. It is also possible to employ a mixture of, for example, spherules having coatings designed to provide differing release times so as to allow pulsed release of the active ingredient.

The terms "active ingredient" includes any material which is or may be sensitive to temperatures above low ambient, for example 20 to 40° C., but also includes materials that are not degraded at temperatures outside this range. The active ingredient could, for example, be a foodstuff, pharmaceutical, electrically conducting component, without limitation. However, it particularly includes any compound or composition useful in human or veterinary medicine in therapy or diagnosis. Therapeutic agents of particular interest have been referred to hereinbefore. In addition to their value in achieving a delayed release of therapeutic agents, particularly in their delivery to the colon as discussed above, the compositions of the invention are also of interest in a diagnostic context, for example in delivering agents such as contrast media to the colon in connection with X-ray and NMR imaging techniques. An alternative diagnostic area lies in the delivery of potentially allergenic foodstuff components to the colon for the diagnosis of allergies.

It will be appreciated that the active compound may be mixed with other carrier materials suitable to its particular use. Thus, particularly for therapeutic use, the active compound will often be mixed with one or more of a bulking agent and a lubricant, for example lactose and magnesium stearate, respectively. Dosages of active compounds for therapeutic use will be as disclosed in the literature, for example in the ABPI Data Sheet Compendium, or may sometimes be less owing to the more efficient delivery of the compound.

One preferred "active compound" is 5-aminosalicylic acid (5-ASA), a drug which is used orally in the treatment of colonic disorders. When free 5-ASA is administered orally, little of the drug reaches the colon as the stomach and small intestine inactive and/or absorb the drug. The present invention provides a composition comprising 5-ASA which can be administered orally with delayed release of a substantial amount of the active ingredient in the colon. The 5-ASA is preferably provided in the form of spherules, suitably spheronized in admixture with microcrystalline cellulose and a minor proportion of an inorganic binder such as bentonite. Other suitable active materials include ephedrine and paracetamol.

BRIEF DESCRIPTION OF THE DRAWINGS

The invention will now be described with reference to the accompanying drawings, in which.

EXAMPLES

Figure 1:
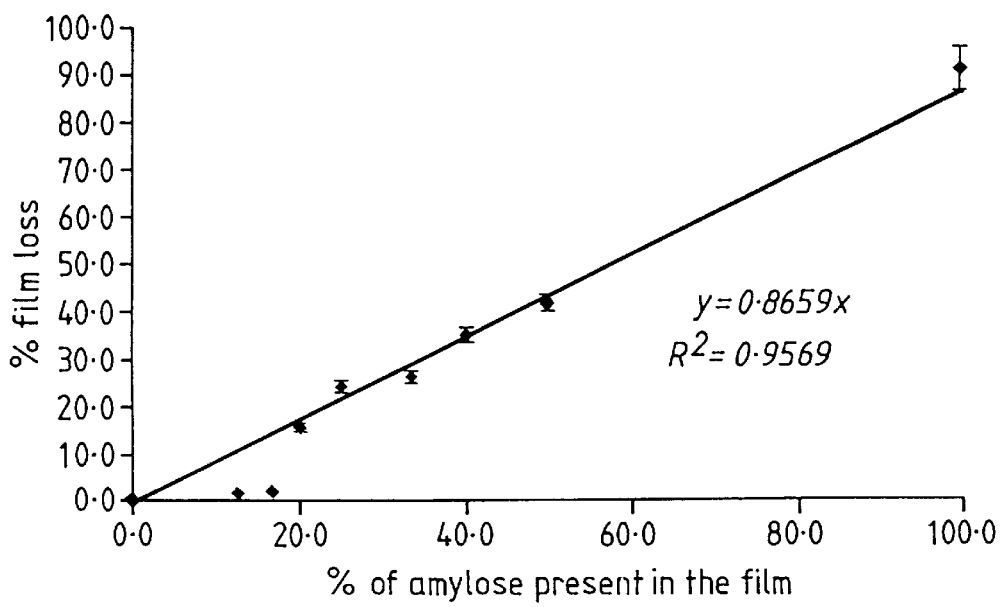
FIG. 1 shows the percentage film loss after 24 hours incubation of film cast from ethanol:water solutions of amylose/ethyl cellulose based on the level of amylose in the mixture.

The invention will now be illustrated further with reference to the following non-limiting examples. Variations on these falling within the scope of the invention will be apparent to a person skilled in the art.

Example 1

1.1 Preliminary Free Film Studies

The organic system was developed using mixture of aqueous dispersion of amylose-butanol complex and organic solutions of ethyl cellulose. Three solvents were selected to form ethyl cellulose solutions. They were ethyl lactate, ethanol and propanol. The mixture systems were investigated for solvent/aqueous compatibility, polymer miscibility and possible influencing factors such as solvent ratio, sold ratio and temperature effect. The study was carried out using free films. The free films formed were subsequently subjected to acid permeability test and in vitro fermentation tests.

1.2 Materials

Ethycellulose, grade N-100, Dow Chemicals

Amylose-butanol complex dispersion, prepared at Institute of Food Research, Norwich, UK Absolute alcohol, general purpose reagegnt Propan-1-ol, AnalaR grade, BDH Merck, UK Ethyl lactate, Aldrich, UK Dibutyl sebacate, Aldrich Chemicals Co. Ltd., UK 1.3 Methods Ethyl lactate, ethanol and propanol were used to make up ethyl cellulose solutions 4.5 g of a 3.33% or 4.67% w/w ethyl cellulose solution was added to 0.5 g of 6% w/w aqueous amylose-butanol complex dispersion, stirred and poured into 9 cm diameter PTFE plates. The films were then allowed to dry at room temperature (~15° C.) and fan-assisted oven (40° C.). Selected films were also tested for digestibility using in vitro fermentation studies described below.

1.4 Results—Amylose

When high amylose ratios were used, the water to solvent ratio in the mixed films increased too. This increases in water content was shown to have drastic influence on the quality of the films produced. In general, the films formed were comparatively more brittle and porous than those obtained using low amylose ratio.

It is essential to determine the exact solvent/water composition where the polymer would precipitate as a gel phase (observed as a semi-transparent jelly-like mass), also known as the Cg (Critical Concentration of Gelation), and below which the polymer began to be insoluble. The value of Cg was precisely determined by the titration method, where water was added dropwise to known quantity of organic ethyl cellulose solution, until the ethyl cellulose solution changed abruptly to cloudy and jelly-like mass appeared. The Cg value was calculated from the amount of organic solvent and the amount of water added. Triangular phase diagrams for the ethyl cellulose-organic solvent-water ternary system for the three solvents used were generated.

The Cg values obtained in this experiment were found to be approximately 62% ethanolic concentration, 54% propanolic concentration and 74% for ethyl lactate. Their values denote the lowest solvent levels require for dissolving ethyl cellulose and subsequent film formation.

1.5 Results—Ethyl cellulose

The same experiment was repeated using amylose-butanol complex instead of ethyl cellulose solution. It was not possible to construct 3-phase diagram for amylose-water-organic solvent systems because amylose dispersion itself is a white, milky dispersion, hence it was difficult to determine the titration end point (the Cg value) where it starts to gel. However, it seems that amylose dispersion is dispersible in these three selected organic solvents in all proportions tested, as no precipitate was formed when organic solvent was added to the amylose dispersion.

From these results testing the individual polymers in the solvent/water mixtures, it was established that the preparation of a mixed film from a single coating liquid containing both the polymers could be achieved using ethanol/water wherein the ethanol was present in at least 70% by weight or propanol/water mixtures in which the solvent was present in at least 60% by weight.

Example 2

Digestibility Investigations of Mixed Films

Mixed solutions containing amylose and ethyl cellulose in varying ratios were generated using the alcohol/water mixtures determined from Example 1 to be suitable for producing the mixed film. Films were cast from a mixed solution containing 5% in total of amylose and ethyl cellulose using the general casting technique described in Example 1.3. After drying, samples of the film were cut and incubated with a predetermined quantity of faecal slurry (same quantity of the same slurry used for each experiment). Following incubation for 24 hours at 37° C., the films are washed with water and dried at 20 C. and 44%RH for 7 days in an incubator and reweighed.

Figure 2:
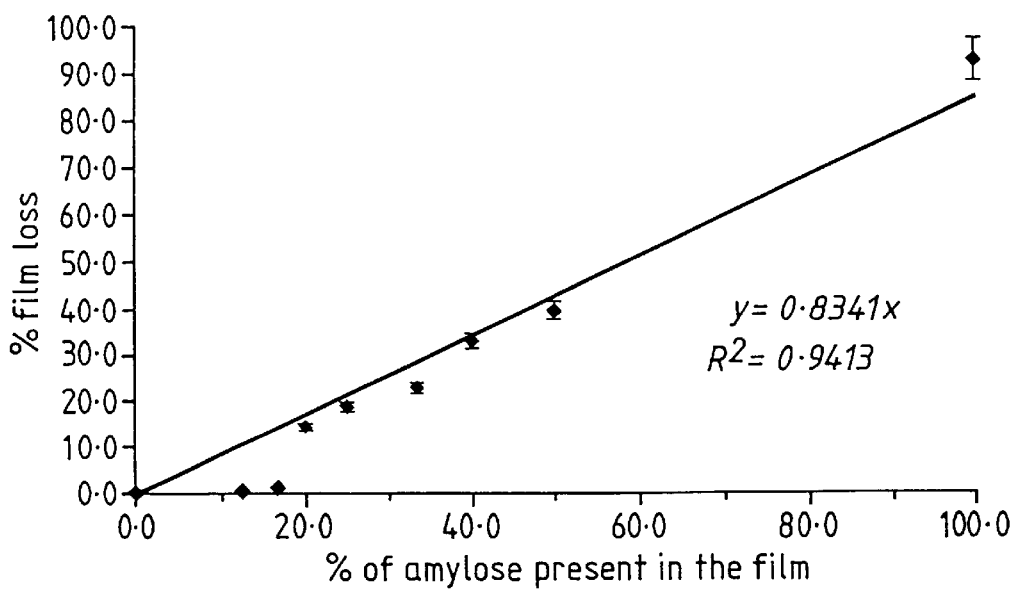
FIG. 2 shows the film loss values based on the level of amylose in the amylose/ethyl cellulose mixture for films cast from propanol:water mixtures.
Figure 3:
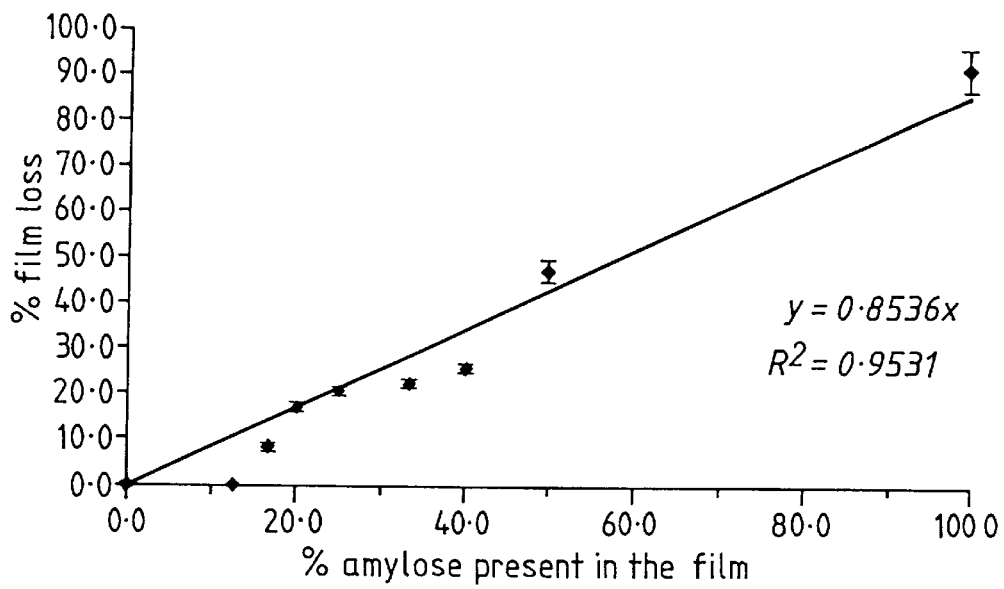
FIG. 3 shows the percentage film loss for similar films case from ethyl acetate.

The results of the digestibility, in terms of the percentage film loss, is shown in FIGS. 1 to 3.

FIG. 1 shows the percentage film loss after 24 hours incubation of film cast from ethanol:water solutions of amylose/ethyl cellulose based on the level of amylose in the mixture.

FIG. 2 shows the film loss values based on the level of amylose in the amylose/ethyl cellulose mixture for films cast from propanol:water mixtures.

FIG. 3 shows the percentage film loss for similar films cast from ethylactate.

From these results it can be seen that the amount of film lost (digested by faecal slurry) increases as the amount of amylose in the film increases. It will, therefore, be appreciated that the rate at which active material is released in the colon will depend upon the amount of amylose in the film.

Example 3

Drug release from coated pellets

Further experiments were carried out using 5-aminosalicyclic acid (hereinafter referred to as 5-ASSA) as a representative at compound used in the therapy of colonic disorders.

General method for preparation of 5ASA-containing spheres

Microcrystalline cellulose (Avice1PH101), lactose, bentonite powder and the active ingredient were mixed for 5 minutes and purified water was added followed by further mixing for 10 minutes. The final mixture contained about 10 weight % 5ASA, 55 weight % MCC, 30% lactose, 5% bentonite plus water. The resulting plastic mass was extruded and the extrudate processed in a spheroniser. The resulting spheres were dried in a fluidised bed for 30 minutes at 60° C. and sieved to obtain spheres having diameters in the range 1.00 to 1.40 mm and a total ASA level of about 10%.

Preparation of Coated Spheres

The spheres obtained above were coated using mixed water/solvent amylose/ethyl cellulose coating composition prepared at a total polymer concentration of 5% by spraying the spheres in a fluidised bed coater at a bed temperature of 35–40° C. to prepare products with varying coating thicknesses (expressed as total weight gain, TWG).

Dissolution of Coatings

The release of 5ASA from the spheres was measured using a quantity of spheres containing a known level of 5ASA into 100 ml dissolution fluid at a temperature of 37° C. and under agitation. The dissolution fluids used were phosphate buffer at pH 7.2 and faecal slurry (10–15%). Samples were taken at 2 hour intervals up to 8 hours and subsequently after 12 hours and 24 hours and analysed by HPLC. For control purposes, uncoated pellets were subjected to the same release tests.

Results

Figure 4:
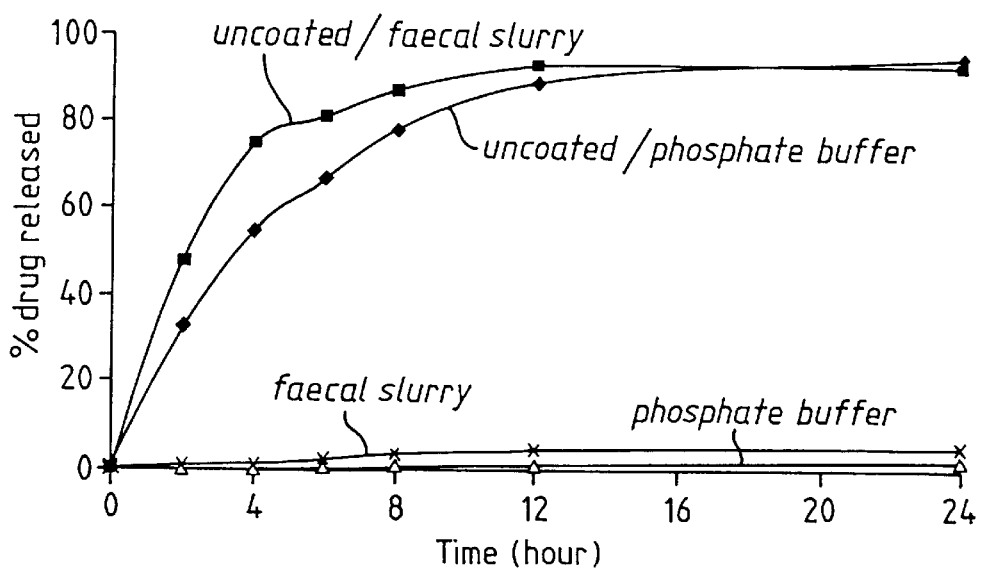
FIG. 4 shows the release profile of spheres which are uncoated and spheres which are coated with a 4:1 ethylcellulose:amylose mixture from the ethyl lactate:water (about 4:1) mixture to a coating level of 3% TWG, in each case into phosphate buffer and faecal slurry.

The results are shown in the accompany figures as follows:

FIG. 4 shows the release profile of spheres which are uncoated and spheres which are coated with a 4:1 ethylcellulose:amylose mixture from an ethyl lactate:water (about 4:1) mixture to a coating level of 3% TWG, in each case into phosphate buffer and faecal slurry.

Figure 5:
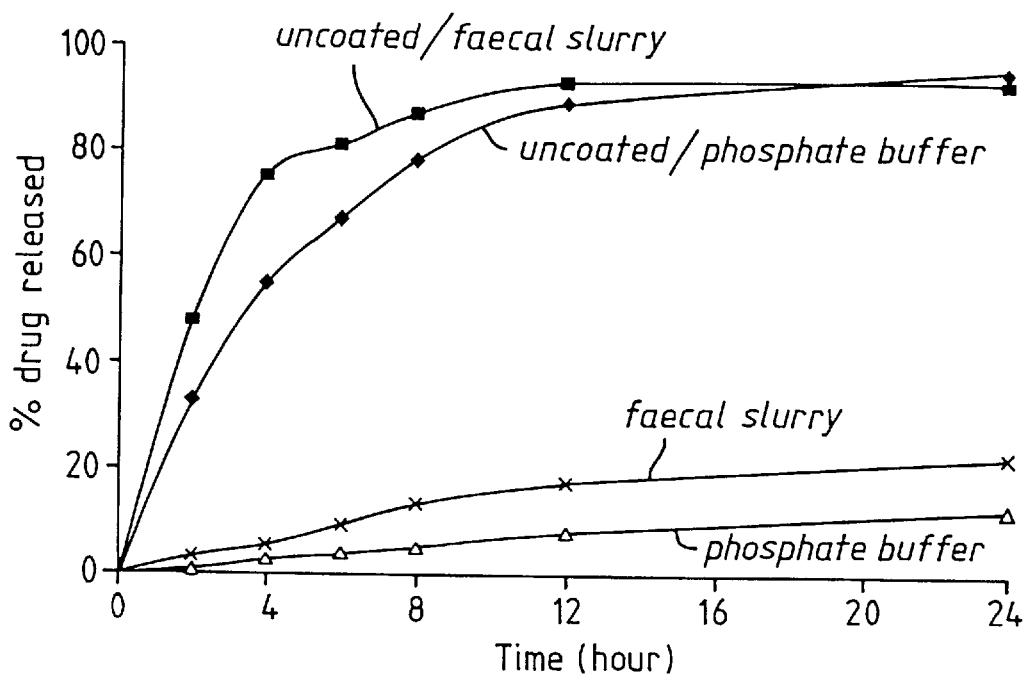
FIG. 5 shows results similar to those in FIG. 4 but using a 2:1 mixture of ethylcellulose:amylose to a total coating level of 6% TWG.

FIG. 5 shows results similar to those in FIG. 4 but using a 2:1 mixture of ethylcellulose:amylose to a total coating level of 6% TWG.

Figure 6:
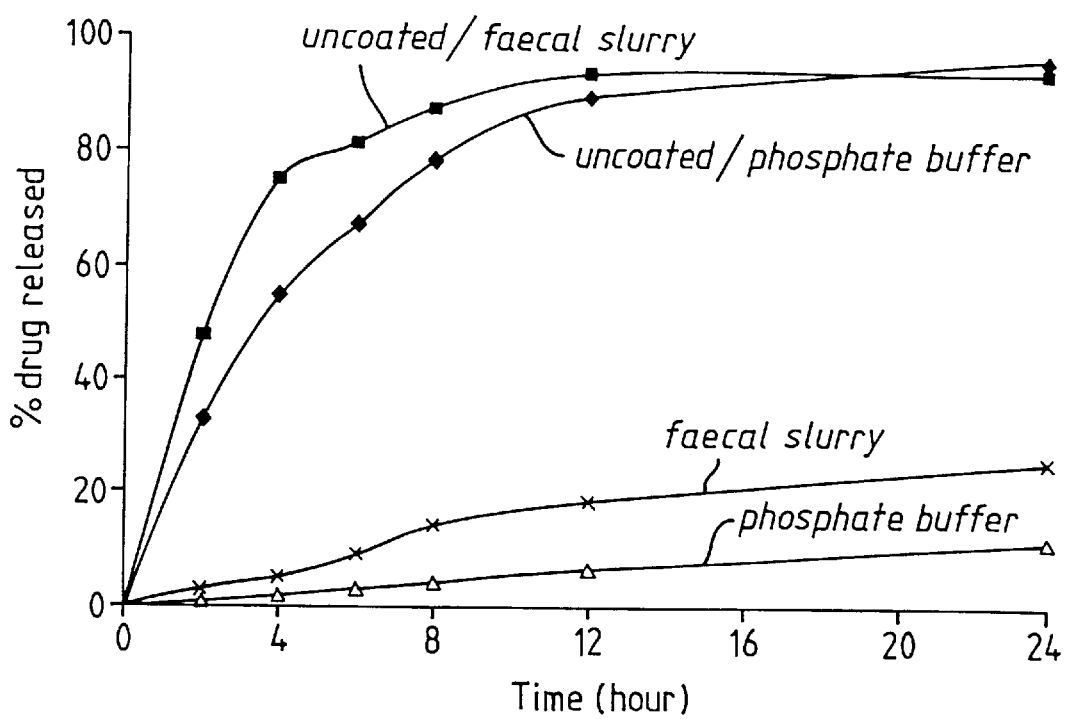
FIG. 6 shows similar results as those in FIG. 4 but using ethyl cellulose:amylose in a ratio 3:2 and to a TWG of 10%.

FIG. 6 shows similar results as those in FIG. 4 but using ethyl cellulose:amylose in a ratio 3:2 and to a TWG of 10%.

Figure 7:
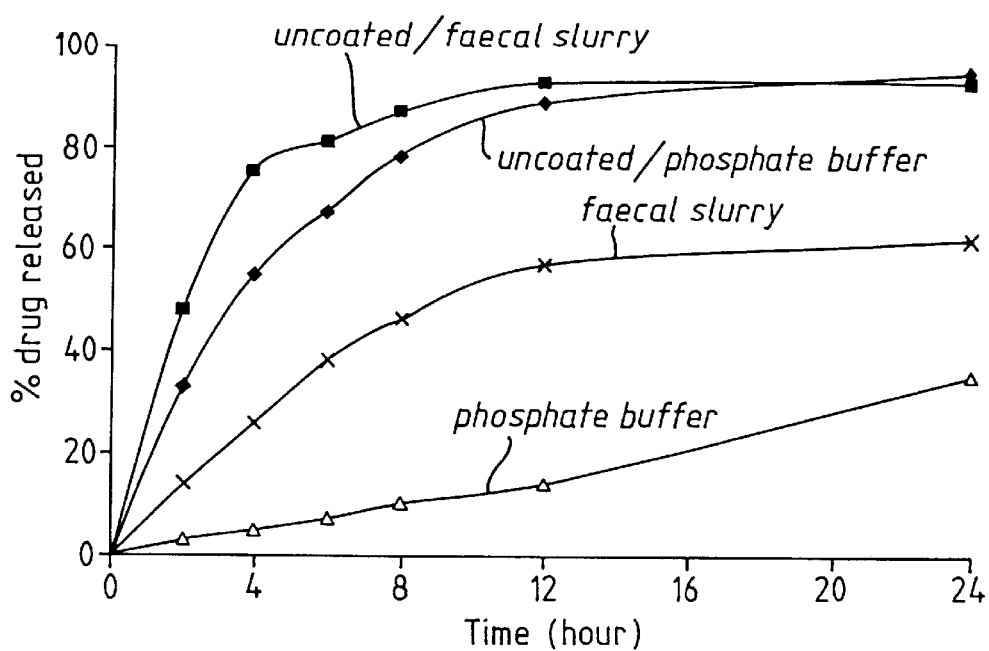
FIG. 7 shows similar results as for FIG. 4, but using ethyl cellulose:amylose 1:1 to a TWG of 15%.

FIG. 7 shows similar results as for FIG. 4, but using ethyl cellulose:amylose 1:1 to a TWG of 15%.

Figure 8:
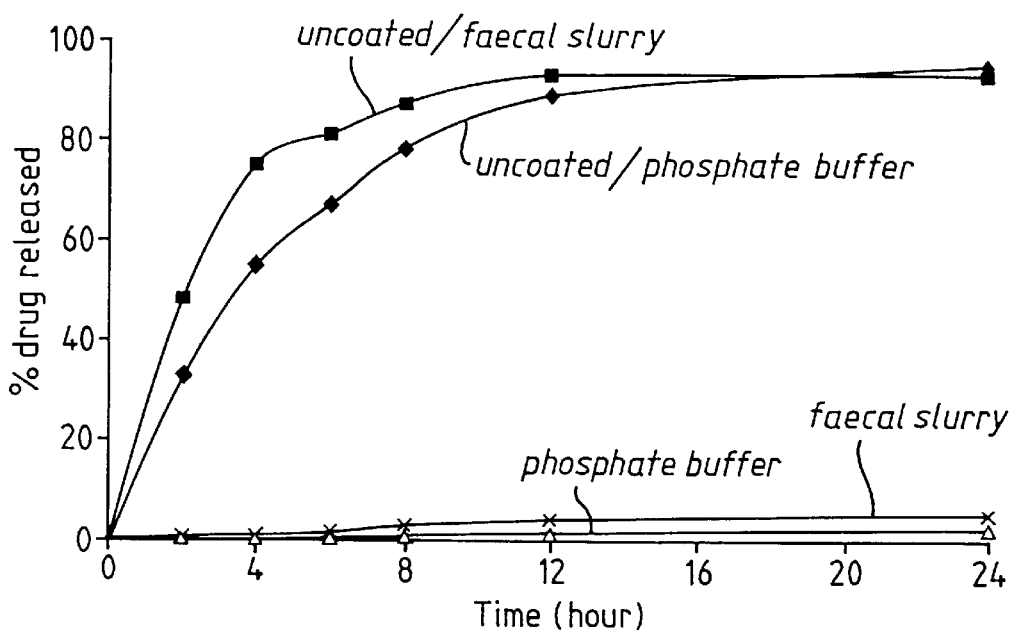
FIG. 8 shows similar results to FIG. 4 but using ethanol in place of ethyl lactate.

FIG. 8 shows similar results to FIG. 4 but using ethanol in place of ethyl lactate.

Figure 9:
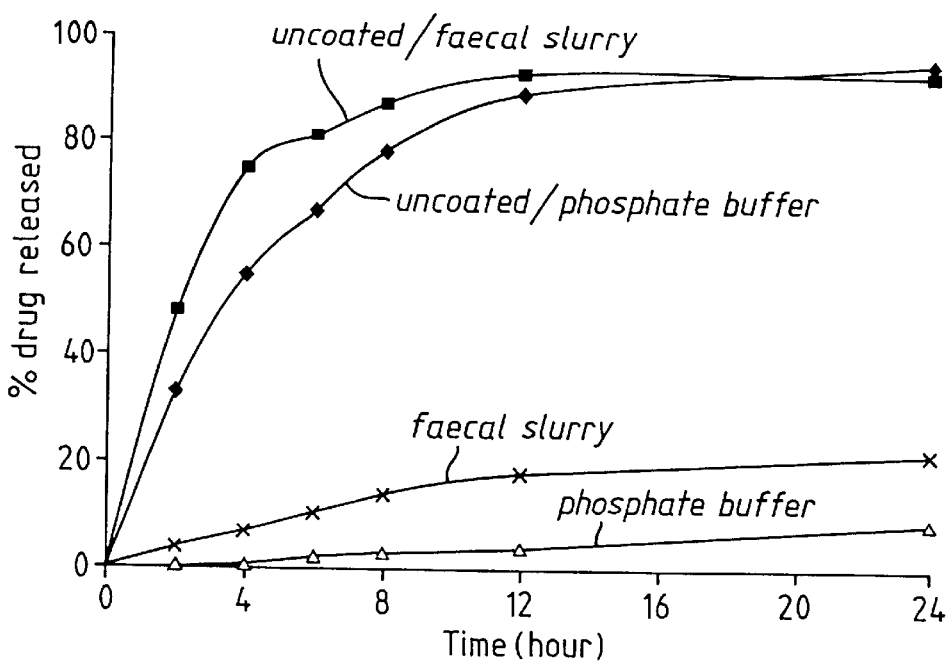
FIG. 9 shows results similar to those of FIG. 6 but using ethanol in place of ethyl lactate.

FIG. 9 shows results similar to those of 6 but using ethanol in place of ethyl lactate.

Figure 10:
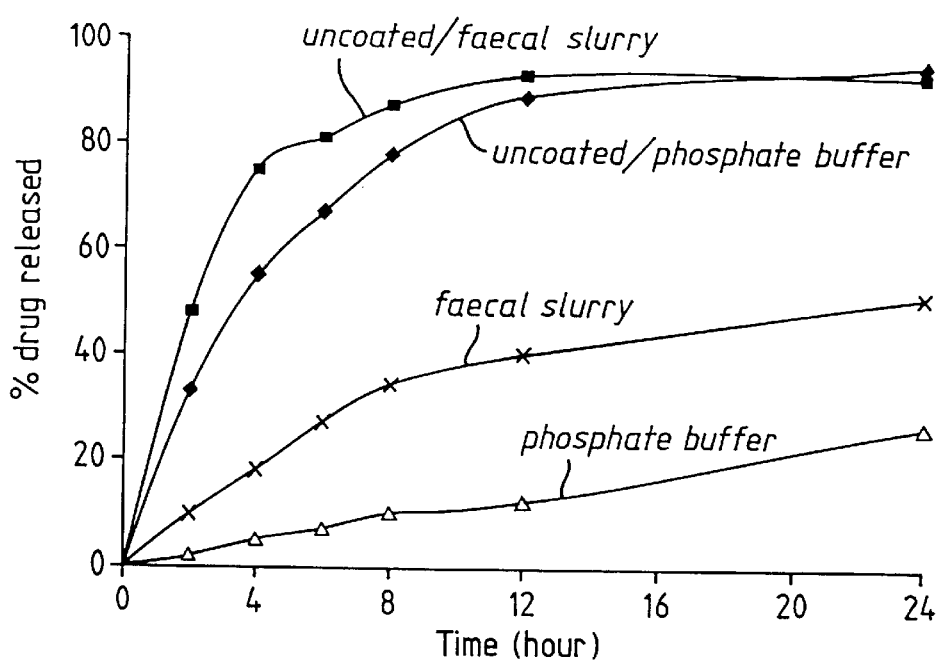
FIG. 10 shows results similar to those of FIG. 7 but using ethanol in place of ethyl lactate.

FIG. 10 shows results similar to those of FIG. 7 but using ethanol in place of ethyl lactate.

Figure 11:
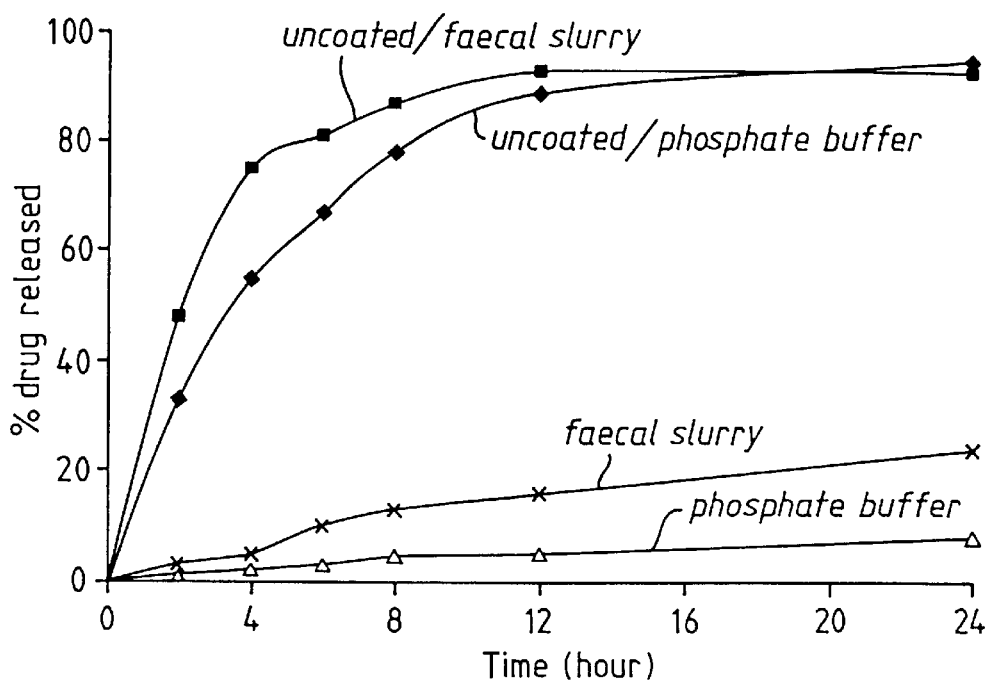
FIG. 11 shows results similar to those of FIG. 5 but using propanol in place of ethyl lactate.

FIG. 11 shows results similar to those of FIG. 5 but using propanol in place of ethyl lactate.

Figure 12:
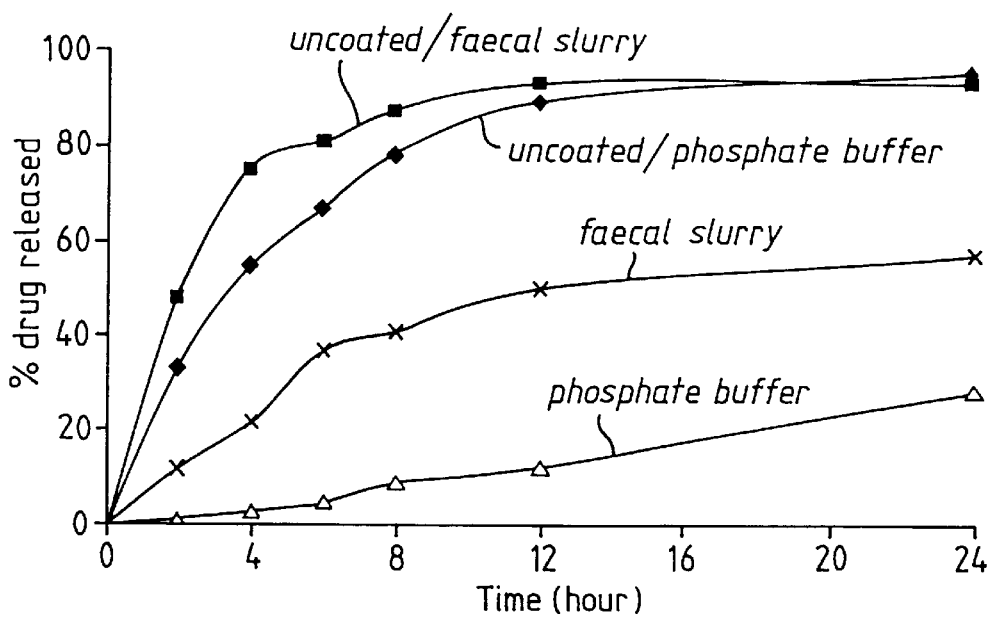
FIG. 12 shows results similar to those of FIG. 7 but using propanol in place of ethyl lactate.

FIG. 12 shows results similar to those of FIG. 7 but using propanol in place of ethyl lactate.

Conclusions

The results show that when ethylcellulose:amylose ratio is high (above 2:1) little significant drug release is observed. This may be due to the absence of continuous amylose channels through the coat surface to the core of the pellet as a consequence of the low amount of amylose present, or due to high tortuosity of the amylose pores which prevent drug diffusion.

Previous studies had shown that where the ratio of amylose within the film coat is raised to above equality with the level of ethyl cellulose, the integrity of the film structure could be compromised. For this reason higher TWG's were used for the experiments using high amylose concentrations. The results where the level of amylose:ethylcellulose is more than 2:3, shows that the relative release in faecal slurry compared to phosphate buffer is increased as desired, indicating that release should not take place in the pre-colonic portions of the gastrointestinal (GI) tract. The degradation of amylose by the enzymes present in the faecal slurry allow adequate release of the active ingredient. Similar results were obtained for paracetamol and ephedrine.

What is claimed is:

1. A method for producing a delayed release composition comprising an active material or a dosage form containing an active material, the method comprising contacting the active material or dosage form containing the active material with a solution of a film-forming composition comprising a mixture of a substantially water-insoluble-film-forming polymer and amylose in a solvent system comprising (1) water and (2) a water-miscible organic solvent which on its own is capable of dissolving the film-forming polymer, and then removing the solvent, wherein the weight ratio of amylose to film-forming polymer is in the range 1:2 to 3:2 and the solvent system contains at least 50% organic solvent.

2. A method according to claim 1, in which the weight ratio of amylose to film-forming polymer is in the range 2:3 to 3:2.

3. A method according to claim 1, which the concentration of amylose in the film-forming composition is such that upon formation of a film, the amylose assumes the glassy state.

4. A method according to claim 1, wherein said film-forming composition comprises film-forming solids in a concentration of between 2 and 8% w/w.

5. A method according to claim 1, in which the insoluble polymer is selected from the group consisting of a cellulosic polymer and an acrylic polymer.

6. A method according to claim 5, in which the cellulosic polymer is ethylcellulose.

7. A method according to claim 1, in which the solvent system contains between 60 and 90% w/w organic solvent.

8. A method according to claim 1, in which the organic solvent is selected from the group consisting of propanol, ethanol and ethyl lactate.

9. A method according to claim 1, in which the active material is contacted with a solution of the film-forming composition at a temperature of up to 60° C.

10. A method according to claim 1, in which the active material is contacted with a solution of the film-forming composition at a temperature of between 20 and 40° C.

11. A method according to claim 9, in which the active material is contacted with a solution of the film-forming composition at a temperature of between 30 and 40° C.

12. A method according to claim 9, in which the active material is contacted with a solution of the film-forming composition at a temperature of between 35 and 40° C.

13. A method according to claim 1, in which contact of the active material with the film-forming composition is effected by spraying.

14. A method according to claim 1, in which the film-forming composition further includes a plasticiser.

15. A method according to claim 1, in which the thickness of the film formed upon contact of the film-forming composition with the active material is between 3 and 20% theoretical weight gain (TWG).

16. A delayed release composition containing an active material or a dosage form containing an active material, prepared by a method according to claim 1.

17. A method of treating a patient having a disorder of the colon which comprises administering a composition according to claim 15.

* * * * *